United States Patent [19]
Thompson

[11] Patent Number: 6,046,806
[45] Date of Patent: Apr. 4, 2000

[54] FLOW-THROUGH CELL CULTURE CHAMBER

[75] Inventor: William L. Thompson, Frederick, Md.

[73] Assignee: The United States of America as represented by the Secretary of the Army, Washington, D.C.

[21] Appl. No.: 09/047,389

[22] Filed: Mar. 25, 1998

[51] Int. Cl.[7] .............................. G01N 21/01; G01N 1/10
[52] U.S. Cl. ............................................ 356/246; 356/244
[58] Field of Search ........................................ 356/244, 246

[56] References Cited

U.S. PATENT DOCUMENTS

| | | | |
|---|---|---|---|
| 2,940,360 | 6/1960 | Carter | 88/40 |
| 2,942,520 | 6/1960 | Rose | 88/40 |
| 3,726,597 | 4/1973 | Dvorak | 356/244 |

OTHER PUBLICATIONS

Poyton, et. al., "A Multipurpose Microperfusion Chamber", Experimental Cell Research 60, pp. 109–114 (1970).

*Primary Examiner*—Frank G. Font
*Assistant Examiner*—Michael P. Stafira
*Attorney, Agent, or Firm*—Charles H. Harris; John Francis Moran

[57] ABSTRACT

Provided is a flow-through cell culture chamber having an internal chamber for containing cultured cells defined in part by transparent cover slips. Fastening and retainer structures are utilized to urge the cover slips towards one another and seal the internal chamber. The retainer structures are constructed and arranged such that when they are drawn towards one another and contact opposing surfaces of the cell culture chamber body, sufficient pressure is provided against the cover slips to seal the internal chamber.

20 Claims, 5 Drawing Sheets

34

20

22

36

32

24

26

28

30

FLOW-THROUGH CELL CULTURE CHAMBER

FIELD OF THE INVENTION

The invention relates to a flow-through cell culture chamber for use in light microscopy.

BACKGROUND OF RELATED ART

Cell culture chambers have been used by biologists to study the growth of cells. By growing cells in a cell culture chamber, cell growth can be continuously observed under a light microscope. Early cell culture chambers utilized concave slides for viewing cell cultures. However, this type of chamber is unsuitable for cells which require continuous replenishment of gas and/or liquid phases of the growth medium. Furthermore, the concave structure of the cell culture chamber introduces undesirable optical effects when viewing the cells under a light microscope. In response, flow-through cell culture chambers have been developed through which aerated growth medium could be continuously supplied.

In order to be suitable for use in most types of light microscopes, the flow-through cell culture chamber should have the following characteristics: (1) optically flat, strain-free, parallel surfaces, with a fixed viewing thickness; (2) a closed culture chamber to safely observe, handle and contain human pathogens or other hazardous materials; (3) an easily sterilizable culture chamber; and (4) the materials forming the walls of the culture chamber should be biologically inert and non-toxic.

A flow-through culture chamber was disclosed in Poynton, et. al., *Experimental Cell Research* 60, pages 109–114 (1970), which utilizes compressible spacers to maintain the space between the glass surfaces of the cell culture chamber. The two pieces of glass are placed on either side of the compressible spacer and then set screws or similar devices are tightened around the periphery of the chamber to produce a seal. However, it is difficult to tighten the screws uniformly to produce a chamber which is strain free and in which the two pieces of glass are parallel. Furthermore, liquid medium is replaced in the chamber by inserting syringes through the compressible spacer, which is undesirable.

U.S. Pat. No. 3,726,597 discloses a flow-through cell culture chamber which is sealed using a compression ring attached to the chamber. Installation of the compression ring requires the use of a special pair of pliers. Installation of the compression ring is very difficult, and often, when installing the compression ring one or both of the cover slips shatter. Furthermore, if the pliers slip, damage can be done to the inlet or outlet tubing to the culture chamber. This type of flow-through cell culture chamber is difficult to clean, assemble, and use on an inverted fluorescent microscope. Thus, there is a need for a simple and efficient flow-through culture chamber.

SUMMARY OF THE INVENTION

An objective of the present invention is to provide a simple and efficient flow-through cell culture chamber which can be easily assembled and disassembled without the use of complicated tools.

Another objective is to provide a flow-through cell culture chamber which is constructed and arranged such that breakage of the cover slips or other parts caused by uneven or over tightening is substantially avoided.

The above objectives and other objectives are obtained by the following. Provided is a novel flow-through cell culture chamber having:

a chamber body having opposing surfaces and an inner wall defining a first aperture through said opposing surfaces;

a spacer having first and second opposing surfaces and a second aperture therethrough which is smaller than the first aperture, the spacer being constructed and arranged to fit within the first aperture and having a predetermined thickness between the opposing surfaces;

a first transparent cover constructed and arranged to fit within the first aperture and cover the second aperture;

a second transparent cover constructed and arranged to fit within the first aperture and cover the second aperture, an internal volume being defined by the first and second covers and the spacer;

a first seal having an aperture and being constructed and arranged to fit within the first aperture and seal at least one of the first transparent cover with the first opposing surface of the spacer or the first transparent cover with the inner wall of the chamber body;

a second seal having an aperture and being constructed and arranged to fit within the first aperture and seal at least one of the second transparent cover with the second opposing surface of the spacer or the transparent cover with the inner wall of the chamber body;

a first retainer structure constructed and arranged to urge the first transparent cover towards the first opposing surface of the spacer, the first retainer structure having a third aperture which is constructed and arranged to align with the second aperture when mounted to the chamber body to allow light to pass through at least a portion of the internal volume;

a second retainer structure constructed and arranged to urge the second transparent cover towards the second opposing surface of the spacer, the second retainer structure having a fourth aperture which is aligned with the second aperture when mounted to the chamber body to allow light to pass through at least a portion of the internal volume;

fastening structure for drawing the first and second retainers towards one another;

an inlet port in the chamber body and the spacer constructed and arranged to allow a liquid to enter the internal volume; and an outlet port in the chamber body and the spacer constructed and arranged to allow a liquid to exit the internal volume, wherein the retainer structures are constructed and arranged such that when the first and second retainer structures are drawn towards one another and contact the opposing surfaces of the chamber body sufficient pressure is provided against the first and second transparent covers and the first and second seals to seal the first transparent cover with at least one of the first opposing surface of the spacer or the inner wall of the chamber body and the second transparent cover with at least one of the second opposing surface of the spacer or the inner wall of the chamber body.

DETAILED DESCRIPTION OF PREFERRED EMBODIMENTS

Figure 1:
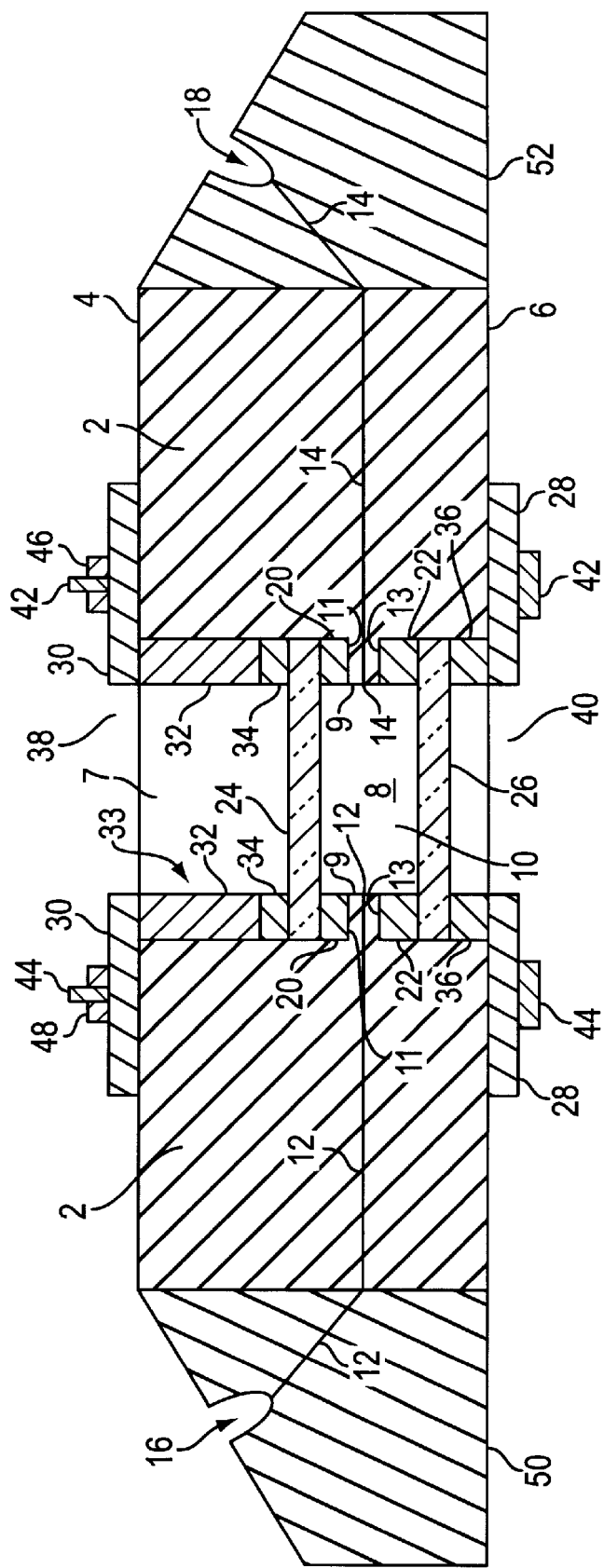
FIG. 1 illustrates a sectional view of an assembled flow-through cell culture chamber according to the present invention.
Figure 2:
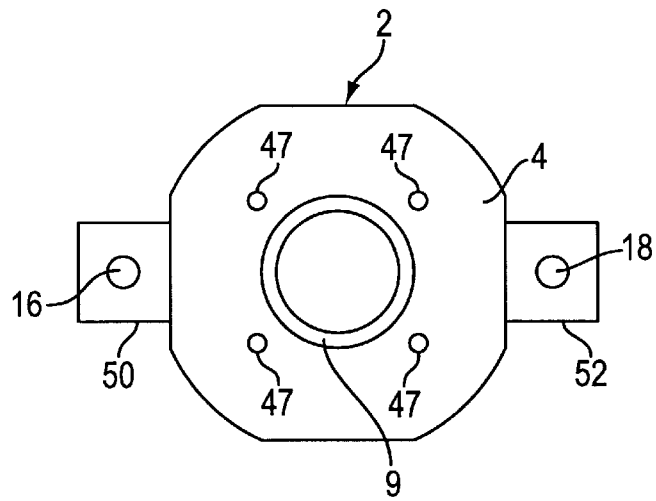
FIGS. 2, 2A through 2I illustrate some of the individual parts of a flow-through cell culture chamber according to the present invention.
Figure 2A:
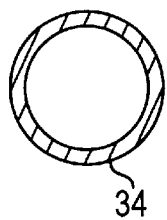
Figure 2B:
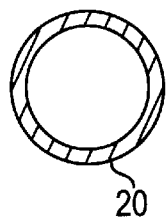
Figure 2C:
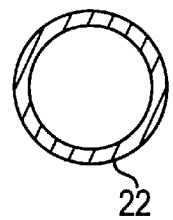
Figure 2D:
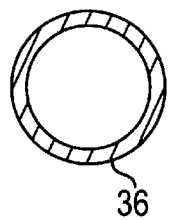
Figure 2E:
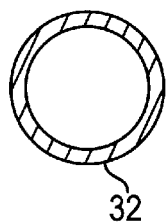
Figure 2F:
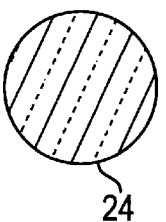
Figure 2G:
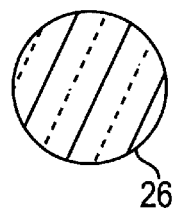
Figure 2H:
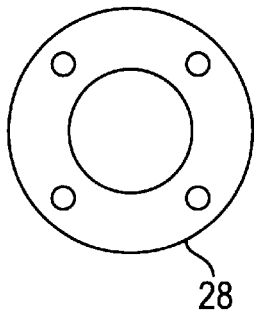
Figure 2I:
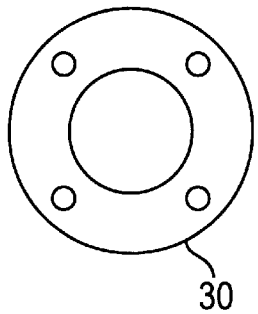

The present invention will now be described in detail with reference to the attached drawings. FIG. 1 illustrates an assembled flow-through cell culture chamber according to the present invention. FIG. 2 illustrates the individual parts of the flow-through cell chamber, except for the fastening structure. The cell culture chamber body shown generally at 2 has opposing surfaces 4 and 6 and a first aperture 7 therethrough. The chamber body 2 can be formed from any suitable material. The material selected should be resistant and non-toxic to the type of cells to be cultured within the cell culture chamber, as well as any microbicides utilized to sterilize the cell culture chamber. Furthermore, the material should be autoclavable. Examples of suitable materials include ceramic, composite, glass, metal and plastic. Preferably, the material is plastic and more preferably polycarbonate plastic.

A spacer 9 is contained within aperture 7. The spacer 9 has a second aperture 8 and comprises the side walls of the internal volume 10. The aperture of the spacer 9 is smaller than the aperture 7. Spacer 9 has opposing surfaces 11 and 13, which should be substantially parallel. Spacer 9 has a predetermined thickness between the opposing surfaces 11 and 13, which at least partially defines the distance between the transparent covers 24 and 26. The distance between the transparent covers 24 and 26 is hereinafter referred to as the thickness of the internal volume 10. The desired predetermined thickness will depend upon the type of light microscopy utilized, the type of cells being cultured, and the type of studies being conducted. Based on the disclosure provided herein, one skilled in the art will easily be able to adjust the predetermined thickness as desired. Preferably, the predetermined thickness is as thin as possible to provide optimum optics and flow dynamics through the internal volume 10, but sufficiently thick to maintain a good nutritional environment and sufficient air for the cultured cells. For most types of light microscopy, the predetermined thickness should be such that the internal volume 10 has a thickness of about 0.2 inches or less, more preferably about 0.1 inches or less. The spacer 9 should be formed from a substantially non-compressible material such as ceramic, composite, glass, plastic or metal. The spacer 9 is preferably integrally formed with the chamber body 2. For example, if plastic is utilized as the material for forming the chamber body 2, the spacer 9 can be integrally formed when the chamber body 2 is molded. If desired, the spacer 9 can be constructed and arranged to be removable from the chamber body 2.

An inlet 12 and outlet 14 are formed in the spacer 9 and chamber body 2 to allow liquid medium to enter and leave the internal volume 10. The inlet 12 includes a conduit which is connected to an inlet connection port 16 for connecting tubing to the cell culture chamber. The outlet 14 includes a conduit which is connected to an outlet connection port 18 for connecting tubing to the chamber body 2. Any suitable means for connecting tubing to the connection ports 16 and 18 can be utilized. For example, the connection ports 16 and 18 can be threaded internally to facilitate connection between the chamber body 2 and threaded tube couplings for connecting tubing to the chamber body 2.

Preferably, the internal volume 10 and the inlet 12 and outlet 14 are constructed and arranged such that fresh medium is substantially uniformly distributed throughout the internal volume 10. The thickness of the internal volume will affect the surface tension of the medium, which affects the flow dynamics of the medium through the internal volume 10. The location of the inlet 12 and outlet 14, as well as the number of inlets 12 and outlets 14, will also affect the flow dynamics through the internal volume 10. Based on the disclosure provided herein one skilled in the art will be able to provide an inlet 12 and outlet 14 which provides suitable flow dynamics though the internal volume 10, based on the predetermined thickness of the internal volume 10 selected. In this manner, cultured cells at various locations in the internal volume 10 will receive substantially equivalent quantities of nutrients and oxygen from the fresh medium being introduced through inlet 12. For a substantially round internal volume, suitable medium flow through the internal volume has been achieved by locating the inlet 12 and outlet 14 substantially opposed to one another. For example, a suitable diameter for the inlet 12 and the outlet 14 has been found to be about 0.0135 inches for a round internal volume of about 0.024 cubic inches in which the spacer 9 has a thickness of about 0.055 inches. The present invention is not limited to this size inlet and outlet, nor a round shaped internal volume. Furthermore, more than one inlet and one outlet can be used, if desired. Based on the disclosure provided herein, one skilled in the art will easily be able to form suitable inlet(s) and outlet(s) for a desired internal volume shape and size, without undue experimentation.

To facilitate ease of construction, the connection ports 16 and 18 and conduits can be formed in separate chamber body parts 50 and 52, and then the chamber body parts 50 and 52 can be secured to the chamber body 2. The chamber body parts 50 and 52 can be secured to the chamber body 2 using adhesives or other non-removable bonds such as welds. If desired, the chamber body parts 50 and 52 can be removably secured to the chamber body using a fastener. Preferably, when the chamber body 2 and the chamber body parts 50 and 52 are formed from plastic, a suitable adhesive is utilized to attach the chamber body parts 50 and 52 to the chamber body 2.

Seals 20 and 22 seal the transparent covers 24 and 26 with the opposing surfaces 11 and 13 of the spacer 9. In this manner, the inner volume 10 can be sealed to prevent loss of containment of any cells cultured therein. The seals 20 and 22 each have an aperture which aligns with the aperture 8. The seals 20 and 22 should be made of a material which is nontoxic and resistant to the type of cells being cultured. Seals are well known in the art and one skilled in the art will easily be able to select the desired sealing material. Examples of suitable materials include, but are not limited to, rubbers, elastomers, fluoroelastomers, soft plastics, and the like. Fluoroelastomers are a preferred material, with tetrafluoroethylene fluorocarbon polymers or fluorinated ethylene-propylene resins being the most preferred. If desired, the seals 20 and 22 can be formed on the opposing surfaces 11 and 13 of the spacer 9 or on the transparent covers 24 and 26. As shown in FIG. 1, the seals 20 and 22 seal the transparent covers 24 and 26 to the spacer 9. Alternatively, seals can be used to seal the transparent covers 24 and 26 with the inner surface of the aperture 7.

The thickness of the seals 20 and 22 will affect the distance between the transparent covers 24 and 26, and therefore should be considered when selecting a predetermined thickness for the spacer 9. The total thickness of the spacer 9 and the seals 20 and 22 should be such that the thickness of the internal volume 10 is suitable for culturing and viewing the selected cells. Suitable internal volume 10 thicknesses have been found to be about 0.2 inches or less, preferably about 0.1 inches or less.

The transparent covers 24 and 26 should be substantially flat and substantially transparent to the wavelength of light utilized in the desired light microscopy. Examples of suitable materials include glass and plastic. Preferably, the transparent covers are glass.

The transparent covers 24 and 26 are held in place against the seals 22 and 24, and the spacer 9, by retaining structures. A first retainer structure includes retainer 28 and seal 36, as well as any other spacers and seals utilized between the transparent cover 26 and the retainer 28. A second retainer structure includes retainer 30, a second spacer 32 having a fifth aperture 33, seal 34, as well as any other spacers and seal utilized between the transparent cover 24 and retainer 30. The retainers 28 and 30 can be formed from any suitable material which is substantially rigid, for example composites, metals, and plastics.

The retainer 28 has a third aperture 40 and the retainer 30 has a fourth aperture 38. The retainers 28 and 30 are drawn together using a fastening structure comprising four bolts and four nuts which are substantially evenly spaced around the perimeter of the apertures 38 and 40. Only two bolts 42 and 44 and two nuts 46 and 48 are shown in FIG. 1. As the bolts and nuts are tightened, the retainers 28 and 30 move towards one another until a maximum position when the retainers 28 and 30 contact the opposing surfaces 4 and 6. At the maximum position, further tightening of the nuts and bolts will not result in substantial movement of the retainers 28 and 30 towards one another. Any suitable fastening structure can be used for drawing the retainers 28 and 30 towards one another. Examples of suitable fastening structures include, but are not limited to, bolts, threaded rods and screws combined with nuts; clamps; hold downs; and bolts or screws which thread into the chamber body. Preferably, the fastening structure is constructed such that the use of complicated tools is not required to assemble and tighten the fastener. More preferably, the fastening structure is constructed such that the fastening structure can be assembled and fully tightened using finger pressure.

The retaining structures are constructed and arranged such that when the maximum position of tightening the retainers 28 and 30 is reached, sufficient pressure is applied to the transparent covers 24 and 26 against the seals 20 and 22 to seal the transparent cover 24 with opposing surface 11 of said spacer 9 and to seal the transparent cover 26 with opposing surface 13 of said spacer 9. The pressure should not be so great as to crack or otherwise deteriorate the integrity of the transparent covers 24 and 26. When the retainers 28 and 30 contact the opposing surfaces 4 and 6, no further pressure can be applied to the transparent covers 24 and 26 and seals 20 and 22. In this manner, over tightening of the retaining structures and loss of integrity of the transparent covers 24 and 26 is substantially avoided. The retaining structures are capable of providing substantially equal pressure to the surfaces of the transparent covers 24 and 26. Furthermore, the transparent covers 24 and 26 are retained in a substantially parallel position by the substantially parallel opposing surfaces 11 and 13 of the spacer 9.

Based on the disclosure provided herein, one skilled in the art will be able to adjust the retaining structures to provide a sufficient level of pressure against the transparent covers 24 and 26 when the retainers 28 and 30 are tightened to the maximum position. For example, the thickness of the spacer 32 and/or the seals 34 and 36 can be increased or decreased as necessary to provide the desired amount of pressure. The spacer 32 can be integrally formed with the retainer 30, and/or a spacer can be integrally formed with the retainer 28. More than one spacer can be utilized and/or a spacer or spacers can be inserted between the seal 36 and retainer 28. Furthermore, seals and/or spacers can be inserted between the retainer 28 and the opposing surface 6 or the retainer 30 and the opposing surface 4.

For example, in the flow-through cell culture chamber shown in FIGS. 1 and 2, the distance between the opposing surface 4 and the spacer 9 is 0.295 inches. The spacer 32 has a thickness of 0.285. The seal 34 has a thickness of 0.005 inches and the seal 20 has a thickness of 0.003 inches. The transparent cover 24 has a thickness of 0.006 inches. Thus, when the retainer 30 is fully tightened, the seals 20 and 34 are compressed 0.004 inches. The distance between the opposing surface 6 and the spacer 9 is 0.01 inches. The seal 36 has a thickness of 0.005 inches and the seal 22 has a thickness of 0.003 inches. The transparent cover 26 has a thickness of 0.006 inches. Thus, when the retainer 28 is fully tightened, the seals 20 and 34 are compressed 0.004 inches.

When the flow-through cell culture chamber is fully assembled, the apertures of each of the seals, spacers and retaining structures are aligned to allow light to pass through the transparent covers 24 and 26 and the internal volume 10 of the flow-through cell culture chamber. In this manner, cells being cultured can be continuously observed using light microscopy.

The flow-through cell culture chamber can be used in the same manner as conventional flow-through cell culture chambers, such as the chamber described in U.S. Pat. No. 3,726,597, the complete disclosure of which is incorporated herein by reference. For example, the desired cells can be grown on a transparent cover 24 or 26 before or after assembly in the flow-through cell culture chamber. The flow-through cell culture chamber is assembled such that the cells grown on the transparent cover 24 or 26 are contained in the internal volume 10. The cell culture medium present in the internal volume 10 can be replenished with fresh medium by using a pump attached to the inlet connection port 16 via tubing for supplying cell culture medium to the internal volume and spent medium removed via tubing attached to the outlet connection port 18.

Figure 3:
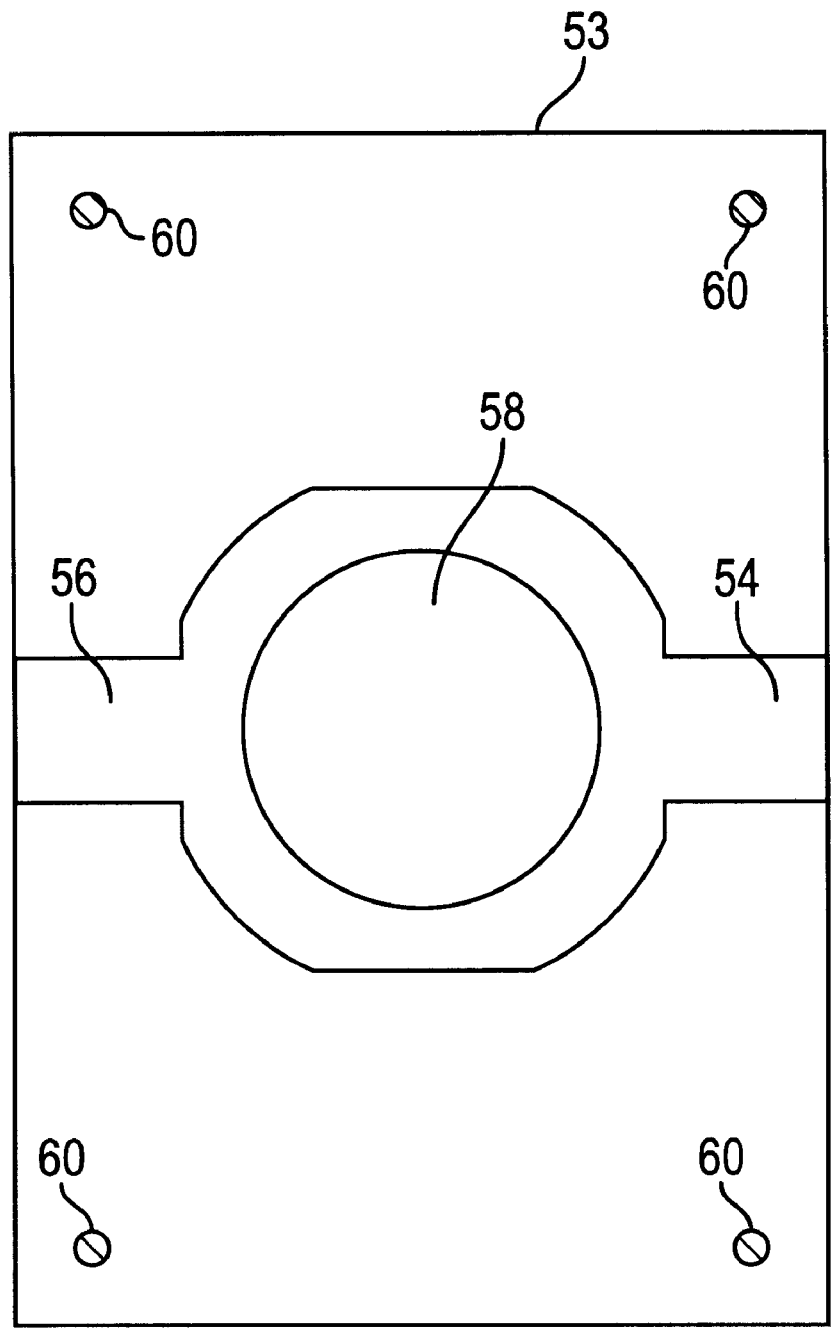
FIG. 3 illustrates a top view of a base plate that is suitable for mounting the flow-through cell culture chamber of the invention to a microscope stage.
Figure 4:
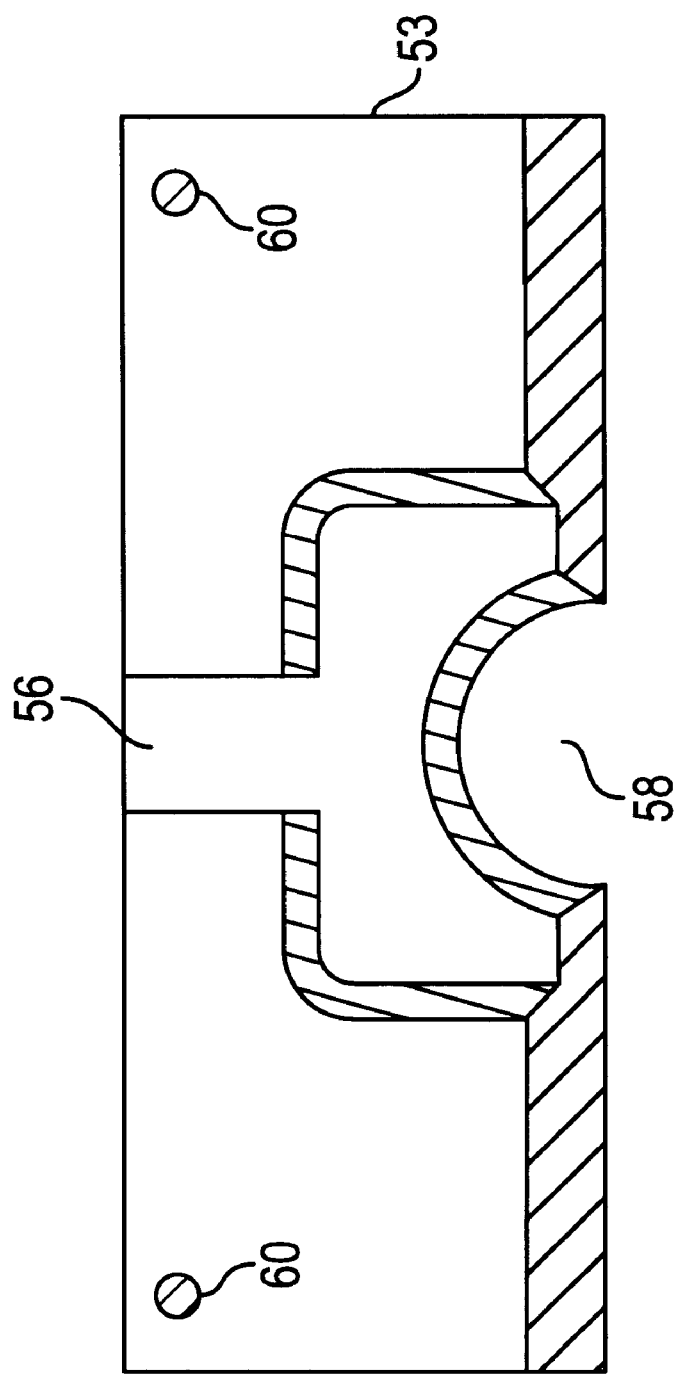
FIG. 4 illustrates an angled sectional view of a base plate that is suitable for mounting the flow-through cell culture chamber of the invention to a microscope stage.
Figure 5:
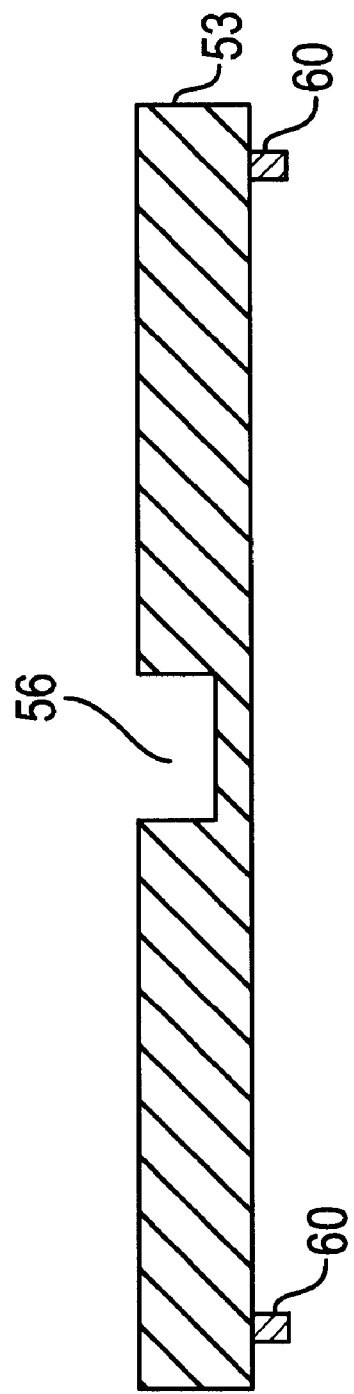
FIG. 5 illustrates a side view of a base plate that is suitable for mounting the flow-through cell culture chamber of the invention to a microscope stage.

The flow-through cell culture chamber can be mounted in a base for attachment to a microscope stage. An example of a suitable base for mounting the flow-through chamber to the stage of a Nikon Phase Inverted Scope is shown in FIGS. 3 through 5. The base plate 53 includes four pegs 60 which line up with holes in the microscope stage for securing the base plate to the microscope stage. The base plate 53 also includes a depression which is constructed and arranged to accept the cell-culture chamber such that the cell-culture chamber lies flat and stable in the depression. The depression includes channels 54 and 56 which accept chamber parts 50 and 52. The depression also includes an aperture 58 for allowing light to pass through the internal volume 10. The aperture 58 can be larger than the retaining structure 28 so that the retaining structure will not affect how the cell-culture chamber lies in the depression. The base plate 53 can be formed from any suitable material, such as composites, metals, plastics, and the like.

While the invention has been described in detail and with reference to specific embodiments thereof, it will be apparent to those of ordinary skill in the art that various changes and modifications can be made to the claimed invention without departing from the spirit and scope thereof.

It is claimed:

1. A flow-through cell culture chamber comprising:

a chamber body having opposing surfaces and an inner wall defining a first aperture through said opposing surfaces;

a spacer having first and second opposing surfaces and a second aperture therethrough which is smaller than said first aperture, said spacer being constructed and arranged to fit within said first aperture and having a predetermined thickness between said opposing surfaces;

a first transparent cover constructed and arranged to fit within said first aperture and cover said second aperture;

a second transparent cover constructed and arranged to fit within said first aperture and cover said second aperture, an internal volume being defined by said first and second covers and said spacer;

a first seal having an aperture and being constructed and arranged to fit within said first aperture and seal at least one of said first transparent cover with said first opposing surface of said spacer or said first transparent cover with said inner wall of said chamber body;

a second seal having an aperture and being constructed and arranged to fit within said first aperture and seal at least one of said second transparent cover with said second opposing surface of said spacer or said second transparent cover with said inner wall of said chamber body;

a first retainer structure constructed and arranged to urge said first transparent cover towards said first opposing surface of said spacer, said first retainer structure having a third aperture which is constructed and arranged to align with said second aperture when mounted to said chamber body to allow light to pass through at least a portion of said internal volume;

a second retainer structure constructed and arranged to urge said second transparent cover towards said second opposing surface of said spacer, said second retainer structure having a fourth aperture which is aligned with said second aperture when mounted to said chamber body to allow light to pass through at least a portion of said internal volume;

fastening structure for drawing said first and second retainers towards one another;

an inlet port in said chamber body and said spacer constructed and arranged to allow a liquid to enter said internal volume; and an outlet port in said chamber body and said spacer constructed and arranged to allow a liquid to exit said internal volume, wherein said retainer structures are constructed and arranged such that when said first and second retainer structures are drawn towards one another and contact respective opposing surfaces of said chamber body sufficient pressure is provided against said first and second transparent covers and said first and second seals to seal said first transparent cover with at least one of a said first opposing surface of said spacer or said inner wall of said chamber body and seal second transparent cover with at least one of a said second opposing surface of said spacer or said inner wall of said chamber body.

2. A flow-through cell culture chamber according to claim 1, wherein said spacer is integrally formed in said chamber body.

3. A flow-through cell culture chamber according to claim 1, wherein said fastening structure comprises nuts and threaded rods, bolts or screws, and said chamber body and retainer structures each having fastener holes.

4. A flow-through cell culture chamber according to claim 3, wherein said fastening structure comprises at least two threaded, screws or bolts.

5. A flow-through cell culture chamber according to claim 1, wherein said chamber body comprises a plastic.

6. A flow-through cell culture chamber according to claim 5, wherein said chamber body comprises a polycarbonate plastic.

7. A flow-through cell culture chamber according to claim 1, wherein said first and second seals are integrally formed on said retaining structure.

8. A flow-through cell culture chamber according to claim 1, wherein said first or second retaining structure further comprises a second spacer constructed and arranged to fit within said first aperture and having a fifth aperture.

9. A flow-through cell culture chamber according to claim 1, wherein said inlet and said outlet are disposed at substantially opposing sides of said spacer.

10. A flow-though cell culture chamber according to claim 1, wherein said spacer is substantially non-compressible.

11. A flow-through cell culture chamber according to claim 1, wherein said first and second seals comprise a material selected from the group consisting of rubbers, elastomers, fluoroelastomers, and soft plastics.

12. A flow-through cell culture chamber according to claim 1, wherein said first and second seals comprise a fluoroelastomer.

13. A flow-through cell culture chamber according to claim 1, wherein said first and second seals comprise a tetrafluoroethylene fluorocarbon polymer or a fluorinated ethylene-propylene resin.

14. A flow-through cell culture chamber comprising:

a plastic chamber body having opposing surfaces and an inner wall defining a first aperture through said opposing surfaces;

a plastic spacer having first and second opposing surfaces and a second aperture therethrough which is smaller than said first aperture, said plastic spacer being integrally formed within said first aperture and having a predetermined thickness between said opposing surfaces;

a first transparent cover constructed and arranged to fit within said first aperture and cover said second aperture;

a second transparent cover constructed and arranged to fit within said first aperture and cover said second aperture, an internal volume being defined by said first and second covers and said plastic spacer;

a first seal having an aperture and being constructed and arranged to fit within said first aperture and seal at least one of said first transparent cover with said first opposing surface of said plastic spacer or said first transparent cover with said inner wall of said chamber body;

a second seal having an aperture and being constructed and arranged to fit within said first aperture and seal at least one of said second transparent cover with said second opposing surface of said plastic spacer or said second transparent cover with said inner wall of said chamber body;

a first retainer structure constructed and arranged to urge said first transparent cover towards said first opposing surface of said plastic spacer, said first retainer structure having a third aperture which is constructed and arranged to align with said second aperture when mounted to said chamber body to allow light to pass through at least a portion of said internal volume;

a second retainer structure constructed and arranged to urge said second transparent cover towards said second opposing surface of said plastic spacer, said second retainer structure having a fourth aperture which is aligned with said second aperture when mounted to said chamber body to allow light to pass through at least a portion of said internal volume;

fastening structure for drawing said first and second retainers towards one another;

an inlet port in said chamber body and said plastic spacer constructed and arranged to allow a liquid to enter said internal volume; and an outlet port in said chamber body and said plastic spacer constructed and arranged to allow a liquid to exit said internal volume, wherein said retainer structures are constructed and arranged such that when said first and second retainer structures are drawn towards one another and contact said opposing surfaces of said chamber body sufficient pressure is provided against said first and second transparent covers and said first and second seals to seal said first transparent cover with at least one of a said first opposing surface of said plastic spacer or said inner wall of said chamber body and seal second transparent cover with at least one of a said second opposing surface of said plastic spacer or said inner wall of said chamber body.

15. A flow-through cell culture chamber according to claim 14, wherein said fastener comprises nuts and threaded rods, bolts or screws, and said chamber body and retainer structures each having fastener holes.

16. A flow-through cell culture chamber according to claim 15, wherein said fastener comprises at least two threaded, screws or bolts.

17. A flow-through cell culture chamber according to claim 14, wherein said chamber body comprises a polycarbonate plastic.

18. A flow-through cell culture chamber according to claim 14, wherein said first and second seals are integrally formed on said retaining structure.

19. A flow-through cell culture chamber according to claim 14, wherein said first or second retaining structure further comprises a second spacer constructed and arranged to fit within said first aperture and having a fifth aperture.

20. A flow-through cell culture chamber according to claim 14, wherein said inlet and said outlet are disposed at substantially opposing sides of said spacer.

* * * * *